(12) United States Patent
Kushnir et al.

(10) Patent No.: US 7,517,319 B2
(45) Date of Patent: Apr. 14, 2009

(54) METHOD AND SYSTEM FOR ANALYZING CARDIOVASCULAR SOUNDS

(75) Inventors: Igal Kushnir, Pardes Hana (IL); Meir Botbol, Pardes Hana (IL)

(73) Assignee: Deepbreeze Ltd., Or Akiva (IL)

( * ) Notice: Subject to any disclaimer, the term of this patent is extended or adjusted under 35 U.S.C. 154(b) by 184 days.

(21) Appl. No.: 10/857,451

(22) Filed: Jun. 1, 2004

(65) Prior Publication Data

US 2004/0267149 A1    Dec. 30, 2004

Related U.S. Application Data

(60) Provisional application No. 60/474,595, filed on Jun. 2, 2003.

(51) Int. Cl.
*A61B 5/0225* (2006.01)
*A61B 5/025* (2006.01)

(52) U.S. Cl. .................. 600/528; 600/493; 600/514

(58) Field of Classification Search ............... 600/528, 600/586, 493, 514
See application file for complete search history.

(56) References Cited

U.S. PATENT DOCUMENTS

| | | | |
|---|---|---|---|
| 3,604,852 A | | 9/1971 | Weintraub |
| 3,878,832 A | * | 4/1975 | Tickner et al. ............ 600/508 |
| 4,220,160 A | * | 9/1980 | Kimball et al. ............ 600/528 |
| 4,289,142 A | | 9/1981 | Kearns |
| 4,387,722 A | | 6/1983 | Kearns |
| 4,777,961 A | | 10/1988 | Saltzman |
| 4,833,625 A | | 5/1989 | Fisher et al. |
| 5,010,889 A | | 4/1991 | Bredesen et al. |
| 5,016,642 A | * | 5/1991 | Dukes et al. ............ 600/509 |
| 5,058,600 A | | 10/1991 | Schechter et al. |
| 5,213,108 A | | 5/1993 | Bredesen et al. |

(Continued)

FOREIGN PATENT DOCUMENTS

GB      2 225 948 A      6/1990

(Continued)

OTHER PUBLICATIONS

Kon et al., "A system for real time Cardiac Acoustic Mapping" Proceedings of the 20th Annual International Conference of the IEEE Engineering in Medicine and Biology Society, vol. 20, No. 1, 1998, 17-20.*

(Continued)

*Primary Examiner*—Carl H. Layno
*Assistant Examiner*—Tammie K Heller
(74) *Attorney, Agent, or Firm*—The Nath Law Group; Jerald L. Meyer; Sung Yeop Chung

(57) ABSTRACT

A method and system for analyzing sounds originating in at least a portion of an individual's cardiovascular system. N transducers, where N is an integer, are fixed on a surface of the individual over the thorax. The ith transducer is fixed at a location $x_i$ and generates an initial signal $P(x_i,i)$ indicative of pressure waves at the location $x_i$, for i=1 to N. the signals $P(x_i,t)$ are processed so as to generate filtered signals in which at least one component of the signals $P(x_i,t)$ not arising from cardiovascular sounds has been removed. The filtered signals may be used for generating an image of the at least portion of the cardiovascular system.

35 Claims, 6 Drawing Sheets

U.S. PATENT DOCUMENTS

| | | | |
|---|---|---|---|
| 5,218,969 A | 6/1993 | Bredesen et al. | |
| 5,285,788 A | 2/1994 | Arenson et al. | |
| 5,309,922 A | 5/1994 | Schechter et al. | |
| 5,492,125 A | 2/1996 | Kim et al. | |
| 5,526,442 A | 6/1996 | Baba et al. | |
| 5,774,558 A | 6/1998 | Drucker | |
| 5,844,997 A | 12/1998 | Murphy, Jr. | |
| 5,957,866 A | 9/1999 | Shapiro et al. | |
| 6,135,960 A | 10/2000 | Holmberg | |
| 6,139,505 A | 10/2000 | Murphy | |
| 6,140,565 A | 10/2000 | Yamauchi et al. | |
| 6,152,884 A | 11/2000 | Bjørgaas | |
| 6,168,568 B1 * | 1/2001 | Gavriely | 600/529 |
| 6,234,963 B1 | 5/2001 | Blike et al. | |
| 6,236,886 B1 | 5/2001 | Cherepenin et al. | |
| 6,341,229 B1 | 1/2002 | Akiva | |
| 6,381,351 B1 | 4/2002 | Powell | |
| 6,396,931 B1 | 5/2002 | Malilay | |
| 6,527,729 B1 * | 3/2003 | Turcott | 600/528 |
| 6,887,208 B2 * | 5/2005 | Kushnir et al. | 600/529 |
| 6,953,436 B2 * | 10/2005 | Watrous et al. | 600/528 |
| 2002/0028006 A1 | 3/2002 | Novak et al. | |
| 2002/0049375 A1 | 4/2002 | Strommer et al. | |
| 2002/0052559 A1 | 5/2002 | Watrous | |
| 2002/0058889 A1 | 5/2002 | Lee | |

FOREIGN PATENT DOCUMENTS

| | | |
|---|---|---|
| JP | 4-82538 | 3/1992 |
| SU | 993917 | 6/1981 |
| WO | 97/29687 A1 | 8/1997 |
| WO | 03/011132 A2 | 2/2003 |

OTHER PUBLICATIONS

"Definition of Cardiovascular system", MedicineNet.com, 1996-2007, http://www.medterms.com/script/main/art.asp?articlekey=11059.*

Benedetto, G., et al., Surface Distribution of Crackling Sounds:, *IEEE Transactions on Biomedical Engineering*, vol. 35, No. 5, pp. 406-412, (1988).

Kompis, M., et al., "Acoustic Imaging of the Human Chest", *Chest*, vol. 120, No. 4, pp. 1309-1321, (2001).

* cited by examiner

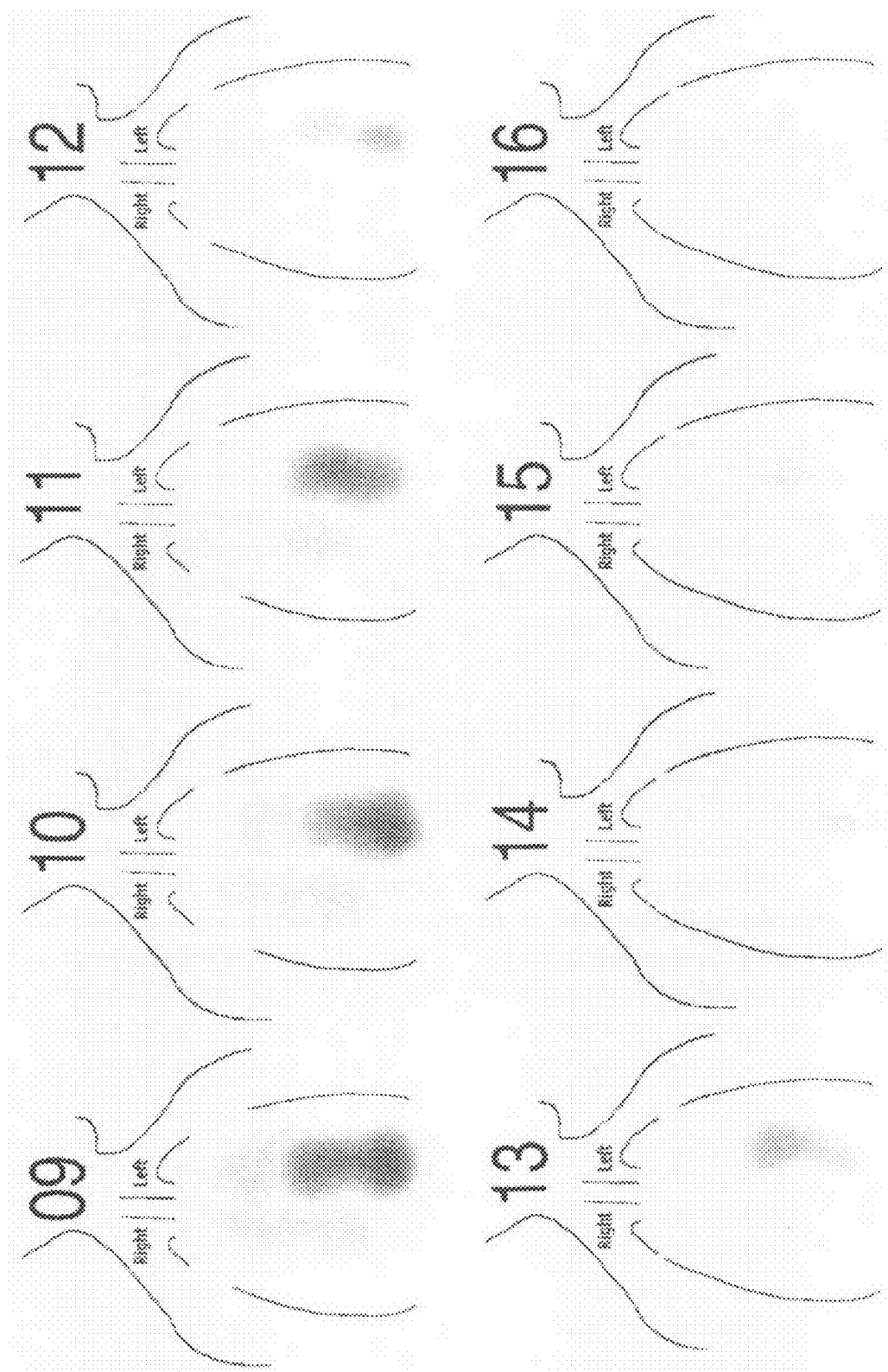
FIG. 5A1

METHOD AND SYSTEM FOR ANALYZING CARDIOVASCULAR SOUNDS

This application claims the benefit of prior U.S. provisional patent application No. 60/474,595 filed Jun. 2, 2003, the contents of which are hereby incorporated by reference in their entirety.

FIELD OF THE INVENTION

This invention relates to medical devices and methods, and more particularly to such devices and methods for analyzing body sounds.

BACKGROUND OF THE INVENTION

Body sounds are routinely used by physicians in the diagnosis of various disorders. A physician may place a stethoscope on a person's chest or back and monitor the patient's breathing or heartbeat in order to detect adventitious (i.e. abnormal or unexpected) lung or heartsounds. The identification and classification of adventitious lung or heart sounds often provides important information about pulmonary or cardiac abnormalities.

It is also known to fix one or more microphones onto a subject's chest or back and to record lung sounds. U.S. Pat. No. 6,139,505 discloses a system in which a plurality of microphones are placed around a patient's chest. The recordings of the microphones during inhalation and expiration are displayed on a screen, or printed on paper. The recordings are then visually examined by a physician in order to detect a pulmonary disorder in the patent. Kompis et al. (Chest, 120 (4), 2001) disclose a system in which M microphones are placed on a patient's chest, and lung sounds are recorded. The recordings generate M linear equations that are solved using a least-squares fit. The solution of the system is used to determine the location in the lungs of the source of a sound detected in the recordings.

U.S. Pat. No. 5,285,788 discloses an ultrasound tissue imaging system having an acoustic transducer, and imaging means for producing an image of tissue. The system also includes Doppler imaging means to produce a scanned acoustic image of moving tissue that is displayed superimposed on the ultrasound image.

SUMMARY OF THE INVENTION

In the following description and set of claims, two explicitly described, calculable, or measurable variables are considered equivalent to each other when the two variables are proportional to one another.

The present invention provides, in one of its embodiments, a system and method for recording and analyzing cardiovascular sounds produced in the cardiovascular system. The system includes a plurality of N transducers (microphones) configured to be attached to an essentially planar region R of the individual's back or chest over the individual's thorax. Positions in the region R are indicated by two-dimensional position vectors $x=(x^1,x^2)$ in a two-dimensional coordinate system defined in the planar region R. The ith transducer, for i=1 to N, is fixed at a position $x_i$ in the region R and generates a signal, denoted herein by $P(x_i,t)$, indicative of pressure waves in the body arriving at $x_i$.

The transducers are typically embedded in a matrix that permits to affix them easily onto the individual's skin. Such a matrix may typically be in the form of a vest or garment for easily placing over the individual's thorax. As may be appreciated, different matrices may be used for differently sized individuals, for different ages, sexes, etc.

The N signals $P(x_i,t)$ are processed by signal processing circuitry. In accordance with the invention, the signals are filtered so as to remove one or more components of the signals not arising from cardiovascular sounds (e.g. respiratory tract signals). Cardiovascular sounds are typically in the range of 6 to 45 Hz, while respiratory tract sounds are typically in the range of 100 to 400 Hz. Thus, respiratory sounds may be removed from the signals by filtering the signals, for example, with a band pass filter passing between 15 to 45 Hz.

The N filtered signals (also indicated herein by $P(x_i,t)$) may be processed in order to diagnose the state of the individual's cardiovascular system. This may be via an automatic differential diagnosis in which the results of the processing are compared to functions or parameters previously stored in a database that are known to be indicative of various disorders in the body region.

The filtered signals may also be processed to generate an image of the individual's cardiovascular system. The results of this processing are displayed on a display device, for example using a gray level scale, as demonstrated in the examples below. In the image, anatomic features of the heart such as the atria, ventricles, septal walls, can be observed. The image may be visually or automatically analyzed for the detection of a disorder in the cardiovascular system similar to the analysis of images obtained by other imaging methods such as X-ray (scintigraphy) or ultrasound imaging (echocardiography).

A region or regions of the heart or cardiovascular system in a displayed image that are suspected of including a pathological condition, may be identified in the image, and this may be in a number of ways, for example, by different colors, by different patterns, by way of a written text, and many other ways. The term "pathological condition" refers to any deviation from the normal, healthy condition of the cardiovascular system. This includes murmurs and other hemodynamic irregularities, cardiac effusion, narrowing of blood vessel, and other space containing lesions in the cardiovascular system, etc.

Additionally, a time interval can be divided into a plurality of sub intervals, and each subinterval processed separately. An image of the cardiovascular system for each of these subintervals may then be determined and displayed sequentially on the display device. This generates a movie showing dynamic changes occurring in the cardiovascular system over the time interval. This allows viewing of the systoles and diastoles of the different parts of the heart during the heartbeat.

In a preferred embodiment, the processing involves determining from the N signals an average acoustic energy arising from cardiovascular sounds, denoted herein by $\tilde{P}(x,t_1,t_2)$, at at least one position x in the region R over a time interval from $t_1$ to $t_2$. The term "acoustic energy" at a location is used herein to refer to a parameter indicative of or approximating the product of the pressure and the mass propagation velocity at that location.

In one embodiment, an average acoustic energy over a time interval from $t_1$ to $t_2$ is obtained at a position of one of the microphones using the algebraic expression $$\tilde{P}(x_i, t_1, t_2) = \int_{t_1}^{t_2} P^2(x_i, t)dt \quad (1)$$

where $x_i$ is the position of the microphone.

In a more preferred embodiment, the processing involves obtaining an average acoustic energy $\tilde{P}(x_i,t_1,t_2)$ over a time interval from $t_1$ to $t_2$ at a plurality of positions $x_i$ of the microphones, for example using Equation (1), and then calculating $\tilde{P}(x,t_1,t_2)$ at other locations x by interpolation of the $\tilde{P}(x_i,t_1,t_2)$ using any known interpolation method.

In a most preferred embodiment, the interpolation is performed to obtain an average acoustic energy $\tilde{P}(x,t_1,t_2)$ at a position $x=(x^1,x^2)$ in the surface R using the algebraic expression:

$$\tilde{P}(x, t_1, t_2) = \sum_{i=1}^{N} \tilde{P}(x_i, t_1, t_2) g(x, x_i, \sigma) \quad (2)$$

where $g(x, x_i, \sigma)$ is a kernel satisfying $$\nabla^2 g = \frac{\partial g}{\partial \sigma} \quad (3)$$

$$\sum_{i=1}^{N} g(x, x_i, \sigma) \text{ is approximately equal to } 1 \quad (4)$$

and where $x_i=(x_i^1, x_i^2)$ is the position of the ith microphone and $\sigma$ is a selectable parameter.

For example, the kernel $$g(x, x_i, \sigma) = \text{Exp} - \left(\frac{(x^1 - x_i^1 \sqrt{\sigma})^2}{2\sigma}\right) \cdot \text{Exp} - \left(\frac{(x^2 - x_i^2 \sqrt{\sigma})^2}{2\sigma}\right) \quad (5)$$

may be used.

The system may optionally contain a display device for displaying the function $\tilde{P}$. The function $\tilde{P}$ may be displayed on the display, for example using a gray level scale, as demonstrated in the examples below. A two dimensional graphical representation of the function $\tilde{P}$ produces an image of the cardiovascular system. In the image anatomic features of the heart such as the atria, ventricles, septal walls, can be observed. The image may be analyzed for the detection of a disorder in the cardiovascular system similar to the analysis of images obtained by other imaging methods such as X-ray (scintigraphy) or ultrasound imaging (echocardiography).

A region or regions of the heart or cardiovascular system in a displayed image that are suspected of including a pathological condition, may de identified in the image, and this may be in a number of ways, for example, by different colors, by different patterns, by way of a written text, and many other ways. The term "pathological condition" refers to any deviation from the normal, healthy condition of the cardiovascular system. This includes murmurs and other hemodynamic irregularities, cardiac effusion, narrowing of blood vessel, and other space containing lesions in the cardiovascular system, etc.

Additionally, a time interval can be divided into a plurality of sub intervals, and an average acoustic energy $\tilde{P}$ determined over the region R for two or more of the sub intervals. An image of $\tilde{P}$ for each of these sub intervals may then be determined and displayed sequentially on the display device. This generates a movie showing dynamic changes occurring in the acoustic energy in the body region, over the time interval. For example, transducers may be placed on a person's chest or back and an average acoustic energy $\tilde{P}$ determined in accordance with the invention for a plurality of sub intervals over one or more heartbeats. An image can be obtained for each of these sub intervals and displayed sequentially so as to generate a movie showing changes in the acoustic energy of the heart over the heartbeat. This allows viewing of the systoles and diastoles of the different parts of the hear during the heartbeat.

The signals $P(x_i,t)$ may also be subjected to additional analysis to detect abnormal heart sounds.

The present invention also provides a program storage device readable by machine, tangibly embodying a program of instructions executable by the machine to perform method steps for determining for at least one time interval, an average acoustic energy function $\tilde{P}$ arising from cardiovascular sounds using an algorithm involving at least one signal $P(xi,t)$ indicative of pressure waves at a location $x_i$ on a body surface.

The present invention still further provides a computer program product comprising a computer useable medium having computer readable program code embodied therein analyzing sounds in at least a portion of an individual's cardiovascular system, the computer program product comprising:

computer readable program code for causing the computer to determine, for at least one time interval, an acoustic energy function $\tilde{P}$ arising from the portion of the cardiovascular system, $\tilde{P}$ being determined in algorithm involving at least one signal $P(xi,t)$ indicative of pressure waves at a location $x_i$ on a body surface.

The invention thus provides a system for analyzing sounds originating in at least a portion of an individual's cardiovascular system comprising:

(One) N transducers, where N is an integer, each transducer configured to be fixed on a surface of the individual over the thorax, the ith transducer being fixed at a location $x_i$ and generating an initial signal $P(x_i,t)$ indicative of pressure waves at the location $x_i$; for i=1 to N; and (Two) a processor configured to receive the signals $P(x_i,t)$ and to filter the signals $P(x_i,t)$ so as to generate filtered signals in which at least one component of the signals $P(x_i,t)$ not arising from cardiovascular sounds has been removed.

The invention thus further provides a system for analyzing sounds originating in at least a portion of an individual's cardiovascular system comprising:

(a) N transducers, where N is an integer, each transducer configured to be fixed on a surface of the individual over the thorax, the ith transducer being fixed at a location $x_i$ and generating an initial signal $P(x_i,t)$ indicative of pressure waves at the location $x_i$; for i=1 to N; and (Two) a processor configured to receive the signals $P(x_i,t)$ and to generate therefrom an image of the at least portion of the cardiovascular system.

The invention thus further provides a method for analyzing sounds originating in at least a portion of an individual's cardiovascular system comprising:

(One) fixing on a surface of the individual over the thorax, N transducers, where N is an integer, the ith transducer being fixed at a location $x_i$ and generating an initial signal $P(x_i,t)$ indicative of pressure waves at the location $x_i$; for i=1 to N; and (Two) processing the signals $P(x_i,t)$ so as to generate filtered signals in which at least one component of the signals $P(x_i,t)$ not arising from cardiovascular sounds has been removed.

The invention thus further provides a method for analyzing sounds originating in at least a portion of an individual's cardiovascular system comprising:

(One) fixing on a surface of the individual over the thorax, N transducers, where N is an integer, the ith transducer being fixed at a location $x_i$ and generating an initial signal $P(x_i,t)$ indicative of pressure waves at the location $x_i$; for i=1 to N; and (Two) processing the signals $P(x_i,t)$ so as to generate therefrom an image of the at least portion of the cardiovascular system.

The invention thus further provides a program storage device readable by machine, tangibly embodying a program of instructions executable by the machine to perform method steps for analyzing sounds originating in at least a portion of an individual's cardiovascular system, comprising: processing N initial signals $P(x_i,t)$, where N is an integer, the initial signals being indicative of pressure waves at a location $x_i$; for i=1 to N, so as to generate filtered signals in which at least one component of the signals $P(x_i,t)$ not arising from cardiovascular sounds has been removed.

The invention thus further provides a computer program product comprising a computer useable medium having computer readable program code embodied therein for analyzing sounds originating in at least a portion of an individual's cardiovascular system, comprising: processing N initial signals $P(x_i,t)$, where N is an integer, the initial signals being indicative of pressure waves at a location $x_i$; for i=1 to N, so as to generate filtered signals in which at least one component of the signals $P(x_i,t)$ not arising from cardiovascular sounds has been removed.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 5A and 5A1 show successive frames from a movie of the heart and lungs of an individual over one respiratory cycle.

DETAILED DESCRIPTION OF THE INVENTION

Figure 1:
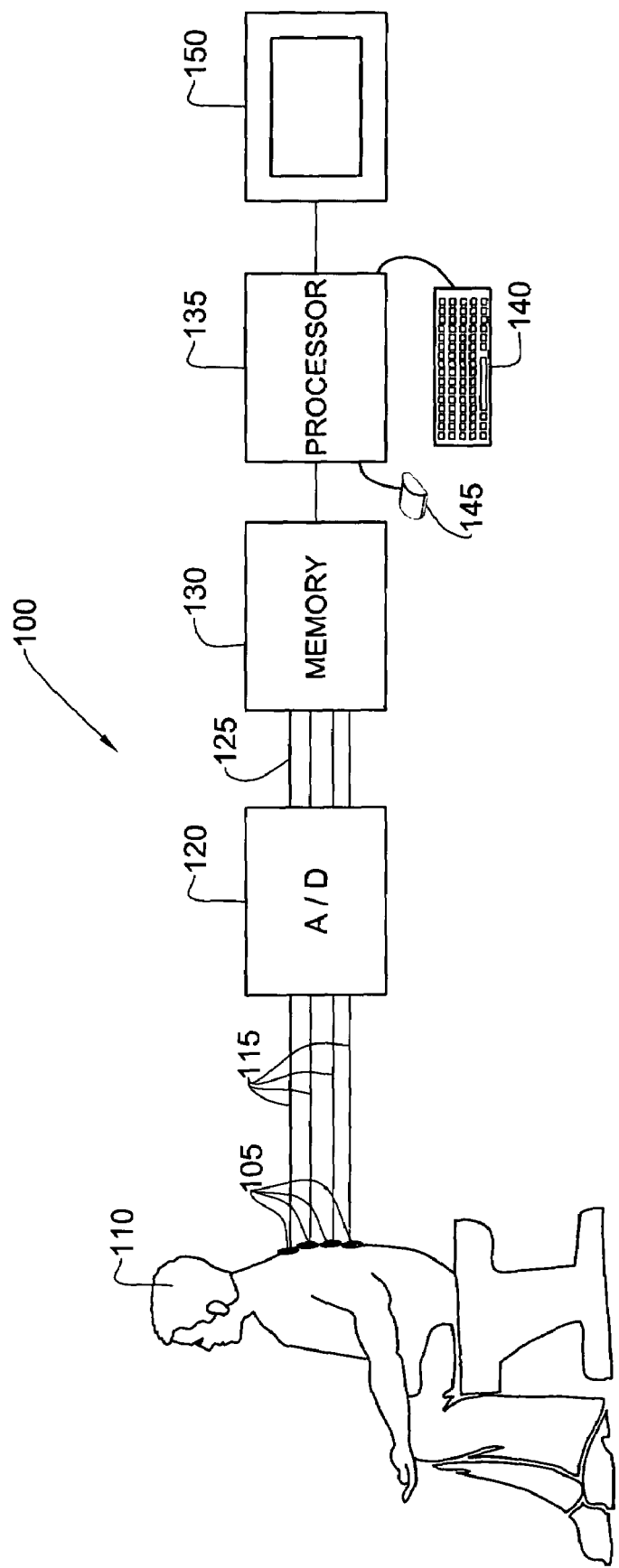
FIG. 1 shows a system for obtaining an analyzing cardiovascular sounds in accordance with one embodiment of the invention.

FIG. 1 shows a system generally indicated by 100 for analyzing body sounds in a three-dimensional region of an individual's body in accordance with one embodiment of the invention. A plurality of N sound transducers 105, of which four are shown, are applied to a planar region of the chest or back skin of individual 110. The transducers 105 may be any type of sound transducer, such as a microphone or a Doppler shift detector. The transducers 105 may be applied to the subject by any means known in the art, for example using an adhesive, suction, or fastening straps. Each transducer 105 produces an analog voltage signal 115 indicative of pressure waves arriving to the transducer. The analog signals 115 are digitized by a multichannel analog to digital converter 120. The digital data signals $P(x_i,t)$ 125, represent the pressure wave at the location $x_i$ of the ith transducer (i=1 to N) at time t. The data signals 125 are input to a memory 130. Data input to the memory 130 are accessed by a processor 135 configured to process the data signals 125. The signals 125 may be denoised by filtering components having frequencies outside of the range of body sounds in the body region, for example, vibrations due to movement of the individual. Each signal 125 may also be subject to band pass filtering so that only components in the signal within the range of cardiovascular sounds are analyzed. The signal may be divided into frequency bands, and each band analyzed separately.

An input device such as a computer keyboard 140 or mouse 145 is used to input relevant information relating to the examination such as personal details of the individual 110. The input device 140 may also be used to input values of the times $t_1$ and $t_2$. Alternatively, the times $t_1$ and $t_2$ may be determined automatically in a respiratory phase analysis of the signals $P(x_i,t)$ performed by the processor 135. The processor 135 determines an average acoustic energy $\tilde{P}(x,t_1,t_2)$ over the time interval from $t_1$ to $t_2$ at least one location x in the region R in a calculation involving at least one of the signals $P(x_i,t)$.

The average acoustic energies are stored in the memory 130 and may be displayed on a display device 150 such as a CRT screen for diagnosis by a physician.

The processor 135 may also perform an automatic differential diagnosis by comparing the function $\tilde{P}$ to functions stored in the memory and known to be indicative of various disorders in the body region.

Figure 2:
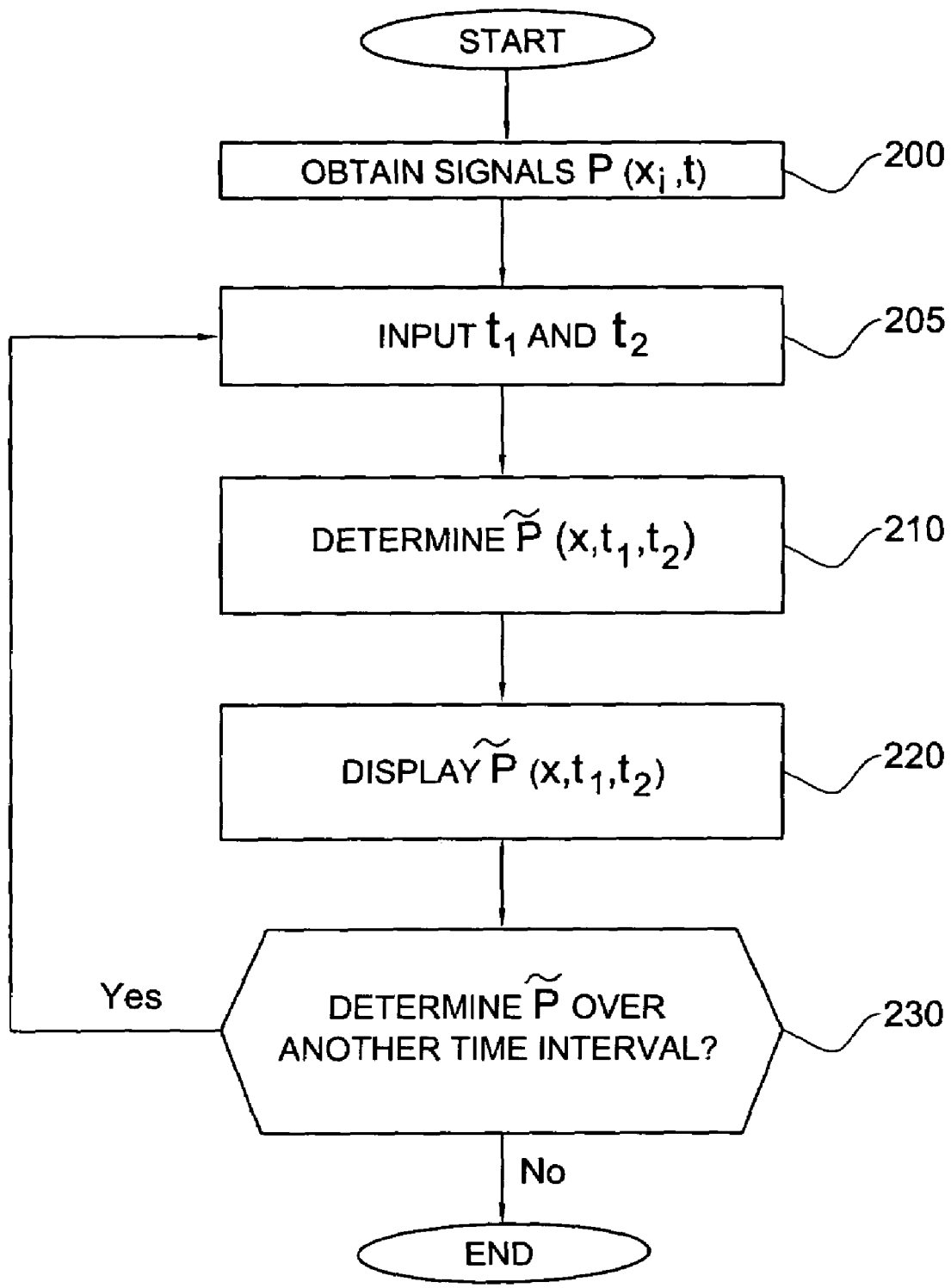
FIG. 2 shows a flow chart for carrying out a method of analyzing cardiovascular sounds in accordance with one embodiment of the invention.

FIG. 2 shows a flow chart diagram for carrying out the method of the invention in accordance with one embodiment. In step 200 the signals $P(x_i,t)$ are obtained from N transducers placed at predetermined locations $x_i$ for i from 1 to N in a region R on the body surface. In step 205 values of $t_1$ and $t_2$ are either input to the processor 135 using the input devices 140 or 145, or are determined by the processor. In step 210, an average acoustic energy $\tilde{P}(x,t_1,t_2)$ is determined at least one location x in the region R over the time interval $t_1$ to $t_2$. In step 220 the average acoustic energy is displayed on the display 150 for at least one value of x. In step 230, it is determined whether a function $\tilde{P}$ is to be determined over another time interval. If yes, the process returns to step 205. If not, the process terminates.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

EXAMPLES

The system and method of the invention were used to analyze cardiovascular sounds in an individual.

Example 1

Figure 3:
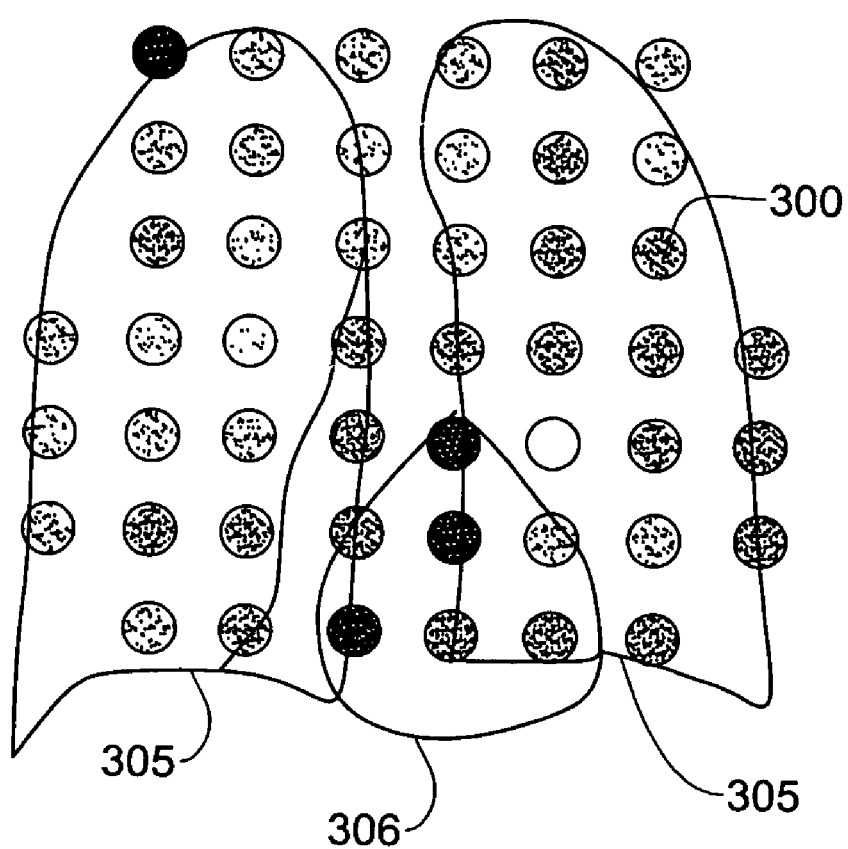
FIG. 3 shows the locations of transducers on an individual's back for analyzing cardiovascular sounds.
Figure 4:
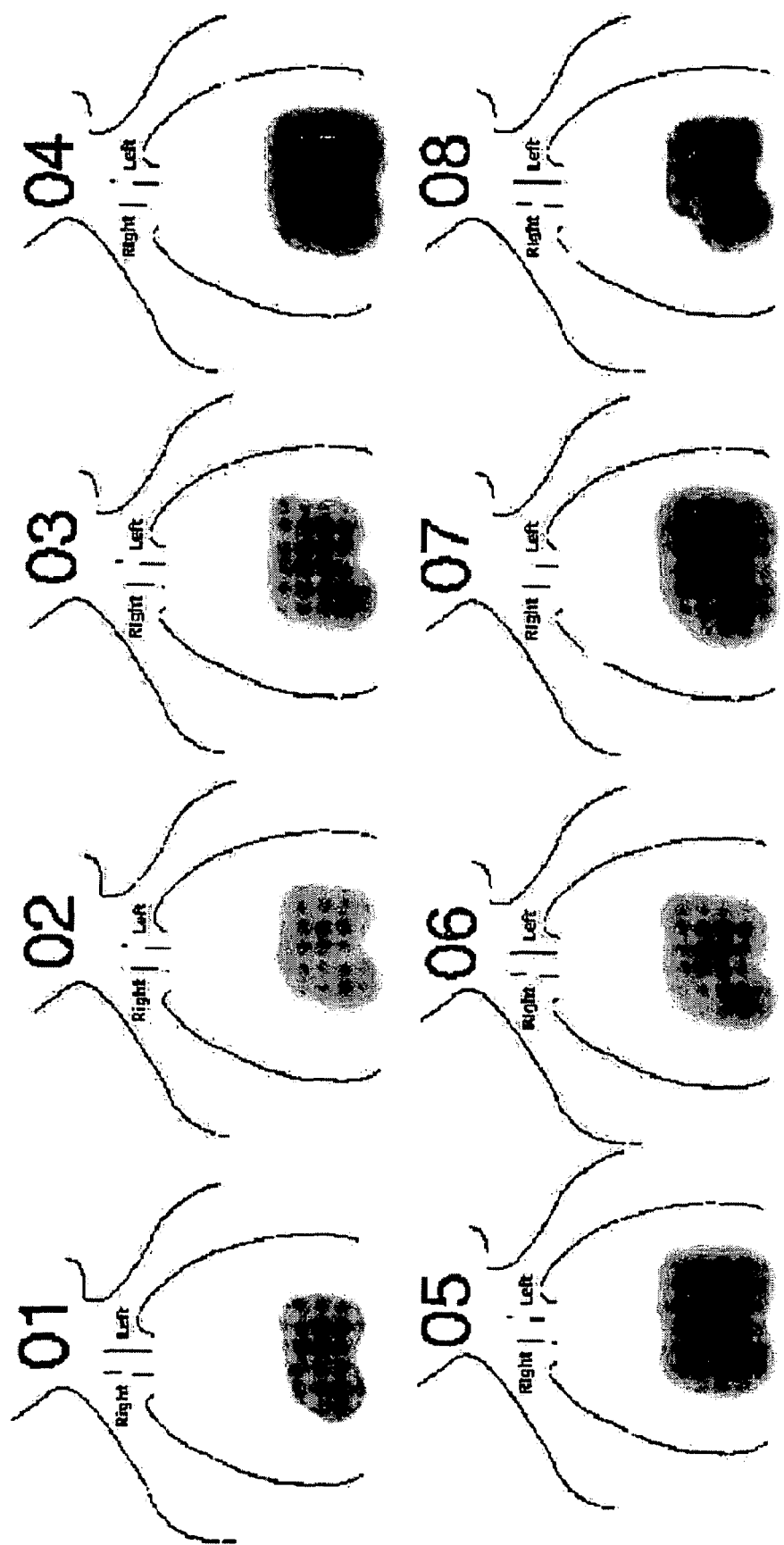
FIG. 4 shows successive frames from a movie of the heart of a healthy individual over one heart beat.

FIG. 3 shows recording of signals over one heartbeat in an individual. A two-dimensional coordinate system was defined on the individual's back. As shown in FIG. 3, 48 transducers were placed on the individual's back over the thorax, at the locations indicated by the circles 300. The curves 305 show the presumed contours of the lungs, and the curve 306 shows the presumed contour of the heart. As can be seen, the transducers were arranged in a regular orthogonal lattice with spacing between the transducers in the horizontal and vertical directions of 2.5 cm. The signals $P(x_i,t)$ from each transducer were then recorded over one heartbeat. Each signal was filtered using a 6-45 Hz band pass filter, in order to remove respiratory tract sounds. The heartbeat was divided into intervals of 0.1 sec duration, and for each interval, $\tilde{P}(x,t_1,t_2)$ was obtained using Equations (1) and (2) above with the kernel g of Equation (5) with σ=36 pixels. FIG. 4 shows the images obtained by representing the obtained functions $\tilde{P}(x,t_1,t_2)$ by gray level shading. The images may be displayed on the display device 150 in rapid succession so as to produce a movie of the heart over a heartbeat. The movie can be analyzed to determine the values of basic parameters of heart function, such as left ventricular end diastolic (LVED) volume, left ventricular end systolic (LVES) volume, right ventricular end diastolic (RVED) volume, right ventricular end systolic (RVES), volume, left atrium end diastolic (LAED) diameter, right atrium end diastolic (LAES) diameter, wall thickness of the inter-ventricular septum (systolic and diastolic), and parameters derivable from these parameters such as left ventricle stroke volume, left ventricular cardiac output, ejection fraction, left ventricular fractional shortening, inter-ventricular septal thickening. The movie can also be analyzed in order to detect heart defects such as valve dysfunction and cardiac arrhythmia.

Example 2

Figure 5A:
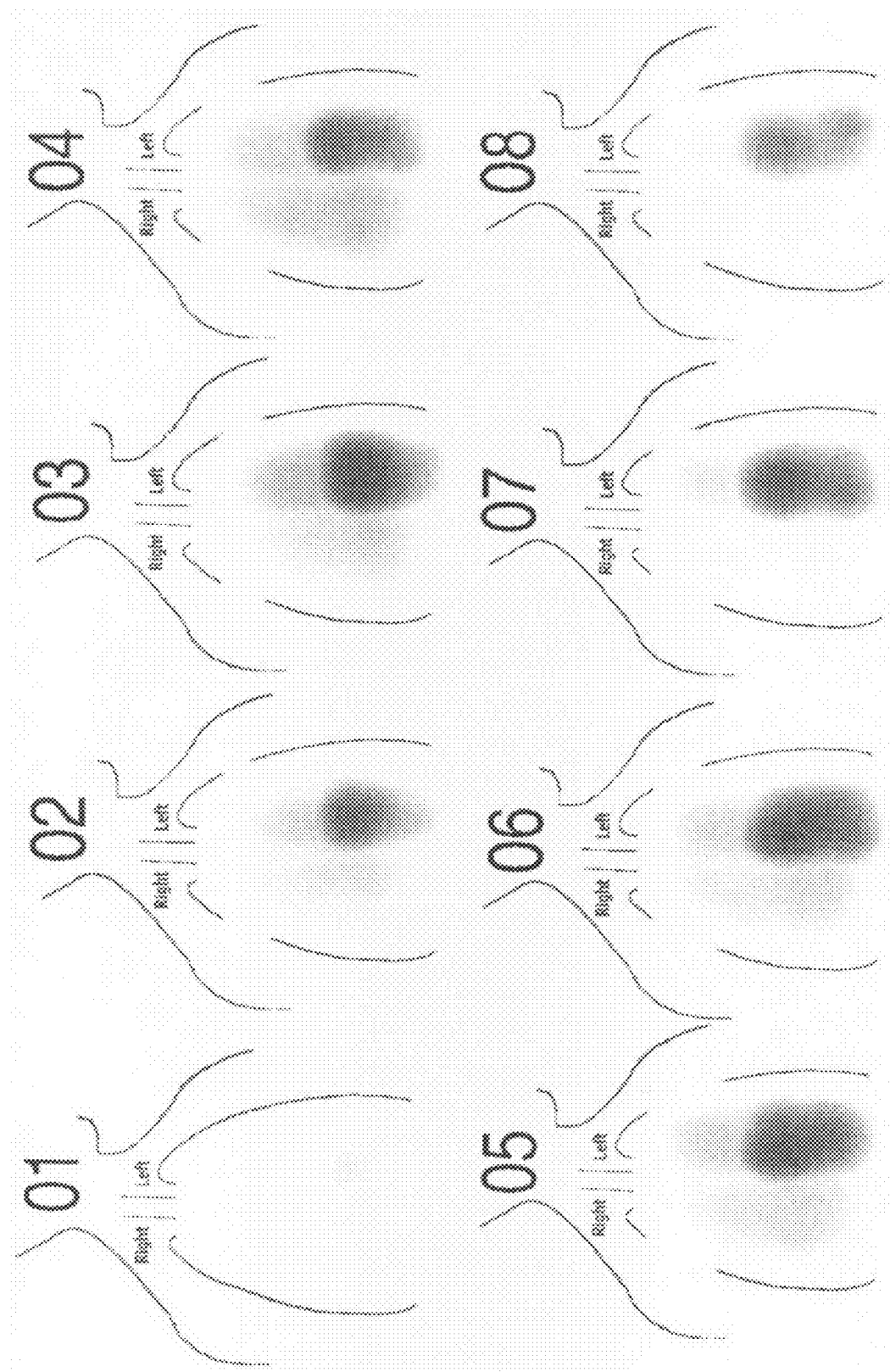

The signals $P(x_i,t)$ were obtained from each transducer as described in Example 1, and were then recorded over one respiratory cycle which includes about 5 heartbeats. Each signal was divided into two sub-signals $P_1(x_i,t)$ and $P_2(x_i,t)$ of different frequency bands. The sub-signal $P_1(x_i,t)$ was obtained by filtering the signal using a 6-40 Hz band pass filter. The sub-signal $P_2(x_i,t)$ was obtained by filtering the signal using a 100-150 band pass filter. The sub-signal $P_1(x_i,t)$ consists primarily of heart sounds, while the sub-signal $P_2(x_i,t)$ consists primarily of lung sounds. The $P_1(x_i,t)$ sub-signal was analyzed by the method of the invention, and the sub-signal $P_2(x_i,t)$ was analyzed as disclosed in Applicant's co-pending U.S. patent application Ser. No. 10/338,742 filed on Jan. 9, 2003. The signal $P_2(x_i,t)$ was divided into intervals of 0.25 sec duration, and the signal $P_1(x_i,t)$ was divided into intervals of 0.1 sec duration. For each interval, functions $\tilde{P}(x,t_1,t_2)$ and $\tilde{P}(x,t_1,t_2)$ were obtained from $P_1(x_i,t)$ and $P_2(x_i,t)$, respectively, using Equations (1) and (2) above with the kernel g of Equation (5) with σ=36 pixels. The two functions are preferably displayed simultaneously on a display device by intensity shading, using a different color for each function. FIG. 5 shows the images obtained by representing the obtained functions $\tilde{P}(x,t_1,t_2)$ and $\tilde{P}(x,t_1,t_2)$ simultaneously by gray level shading. The images may be displayed on the display device 150 in rapid succession so as to produce a movie of the heart over a heartbeat. The movie can be analyzed to determine the values of parameters of heart function, such as cardiac output and blood ejection fraction. The movie can also be analyzed in order to detect hear defects such as valve dysfunction and cardiac arrhythmia.

The invention claimed is:

1. A system for analyzing sounds originating in at least a portion of an individual's cardiovascular system comprising:
   (One) N transducers, where N is an integer, each transducer configured to be fixed on a surface of the individual over the thorax, the ith transducer being fixed at a location $x_i$ and generating an initial signal $P(x_i,t)$ indicative of pressure waves at the location $x_i$, for i=1 to N; and
   (Two) a processor configured to receive the signals $P(x_i,t)$ and to filter the signals $P(x_i,t)$ so as to generate filtered signals in which at least one component of the signals $P(x_i,t)$ not arising from cardiovascular sounds has been removed
   wherein respiratory tract sounds have been removed, and
   wherein the processor is further configured to determine an average acoustic energy $\tilde{P}(x,t_1,t_2)$ arising from the cardiovascular system at at least one position x over a time interval from a first time $t_1$ to a second time $t_2$, $\tilde{P}$ being determined in an algorithm involving at least one of the processed signals,
   wherein the function $\tilde{P}$ is determined at one or more locations x in an algorithm comprising:
   (One) determining an average acoustic energy $\tilde{P}(x_i,t_1,t_2)$ over a time interval from $t_1$ to $t_2$ at a plurality of locations $x_i$ of transducers; and
   (Two) determining an average acoustic energy $\tilde{P}(x,t_1,t_2)$ at at least one location x by interpolation of the determined $\tilde{P}(x_i,t_1,t_2)$.

2. The method according to claim 1 wherein the initial signals are filtered by a band pass filter passing between 15 to 45 Hz.

3. The system according to claim 1 wherein the processor is further configured to generate an image of the at least portion of the cardiovascular system from at least one of the filtered signals.

4. The system according to claim 3 wherein the processor is further configured to display an image of the at least portion of the cardiovascular system on a display device.

5. The system according to claim 1 wherein the processor is configured to generate an image of the at least portion of the cardiovascular system at a plurality of times or over a plurality of successive time intervals, and to display the images successively on a display device.

6. The system according to claim 1 further comprising a two-dimensional display device.

7. The system according to claim 1 wherein the processor is further configured to compare the average acoustic energy $\tilde{P}$ to one or more predetermined functions $\tilde{F}$ and determine a function $\tilde{F}_0$ from among the functions $\tilde{F}$ most similar to $\tilde{P}$.

8. The system according to claim 7 wherein the processor is further configured to make a diagnosis based upon the determined function.

9. The system according to claim 1 wherein the average acoustic energy $\tilde{P}$ over a time interval from $t_1$ to $t_2$ is determined at a location $x_i$ of a transducer using the algebraic expression:

$$\tilde{P}(x_i, t_1, t_2) = \int_{t_1}^{t_2} P^2(x_i, t)dt.$$

10. The system according to claim 1 wherein the average acoustic energy is determined at at least one location x by interpolation of the determined $\tilde{P}(x_i,t_1,t_2)$ using the algebraic expression:

$$\tilde{P}(x, t_1, t_2) = \sum_{i=1}^{N} \tilde{P}(x_i, t_1, t_2) g(x, x_i, \sigma) \quad (2)$$

where $g(x,x_i,\sigma)$ is a kernel satisfying $$\nabla^2 g = \frac{\partial g}{\partial \sigma} \quad (3)$$

$$\sum_{i=1}^{N} g(x, x_i, \sigma) \text{ is approximately equal to 1.} \quad (4)$$

11. The system according to claim 10 wherein $g(x,v_i,\sigma)$ is the kernel $$g(x, x_i, \sigma) = \text{Exp} - \left( \frac{(x^1 - x_i^1 \sqrt{\sigma})^2}{2\sigma} \right) \cdot \text{Exp} - \left( \frac{(x^2 - x_i^2 \sqrt{\sigma})^2}{2\sigma} \right). \quad (5)$$

12. The system according to claim 8 wherein the processor is further configured to display the average acoustic energy $\tilde{P}(x,t_1,t_2)$ on a display device.

13. The system according to claim 1 wherein the processor is configured to determine an average acoustic energy over a plurality of successive time intervals, each average acoustic energy being determined using an algorithm involving at least one of the signals $P(x_i,t)$.

14. The system according to claim 13 wherein the processor is configured to sequentially display on a display device a representation of each determined average acoustic energy.

15. The system according to claim 1, wherein the processor is further configured to
subject the signals $P(x_i,t_1,t_2)$ to band pass filtering in each of one or more frequency bands; and
determine the average acoustic energy function for each frequency band based upon at least one of the filter signals.

16. The system according to claim 15 wherein the processor is configured to display one or more of the average acoustic energy functions determined for a frequency band on a display device.

17. A method for analyzing sounds originating in at least a portion of an individual's cardiovascular system comprising:
(One) fixing on a surface of the individual over the thorax, N transducers, where N is an integer, and for i=1 to N, the ith transducer being fixed at a location $x_i$ and generating an initial signal $P(x_i, t)$ indicative of pressure waves at the location $x_i$;
(Two) processing the signals $P(x_i,t)$ so as to generate filtered signals in which at least one component of the signals $P(x_i,t)$ not arising from cardiovascular sounds has been removed and (Three) determining an average acoustic energy $\tilde{P}(x,t_1,t_2)$ arising from the cardiovascular system at at least one position x over a time interval from a first time $t_1$ to a second time $t_2$, $\tilde{P}$ being determined in an algorithm involving at least one of the processed signals,
wherein the function $\tilde{P}$ is determined at one or more locations x in an algorithm comprising:
(One) determining an average acoustic energy $\tilde{P}(x_i,t_1,t_2)$ over a time interval from $t_1$ to $t_2$ at a plurality of locations $x_i$ of transducers; and
(Two) determining an average acoustic energy $\tilde{P}(x,t_1,t_2)$ at at least one location x by interpolation of the determined $\tilde{P}(x_i,t_1,t_2)$.

18. The method according to claim 17 wherein respiratory tract sounds are filtered from the initial signals.

19. The method according to claim 17 wherein the initial signals are filtered by a band pass filter passing between 15 to 45 Hz.

20. The method according to claim 17 further comprising generating an image of the at least portion of the cardiovascular method from at least one of the filtered signals.

21. The method according to claim 20 further comprising displaying an image of the at least portion of the cardiovascular system on a display device.

22. The method according to claim 17 further comprising generating an image of the at least portion of the cardiovascular method at a plurality of times or over a plurality of successive time intervals, and displaying the images successively on a display device.

23. The method according to claim 17 further comprising comparing the average acoustic energy $\tilde{P}$ to one or more predetermined functions $\tilde{F}$ and determining a function $\tilde{F}_0$ from among the functions $\tilde{F}$ most similar to $\tilde{P}$.

24. The method according to claim 23 wherein the processor is further configured to make a diagnosis based upon the determined function.

25. The method according to claim 17 wherein the average acoustic energy $\tilde{P}(x_i,t_1,t_2)$ is determined over a time interval from $t_1$ to $t_2$ at a plurality of locations $x_i$ of transducers using the algebraic expression:

$$\tilde{P}(x_i, t_1, t_2) = \int_{t_2}^{t_2} P^2(x_i, t)dt.$$

26. The method according to claim 17 wherein the average acoustic energy is determined at at least one location x by interpolation of the determined $\tilde{P}(x_i,t_1,t_2)$ using the algebraic expression:

$$\tilde{P}(x_i, t_1, t_2) = \sum_{i=1}^{N} \tilde{P}(x_i, t_1, t_2) g(x, x_i, \sigma) \quad (2)$$

where $g(x,x_i,\sigma)$ is a kernel satisfying $$\nabla^2 g = \frac{\partial g}{\partial \sigma} \quad (3)$$

-continued $$\sum_{i=1}^{N} g(x, x_i, \sigma) \text{ is approximately equal to 1.} \quad (4)$$

27. The method according to claim 26 wherein $g(x,v_i,\sigma)$ is the kernel $$g(x, x_i, \sigma) = \mathrm{Exp} - \left( \frac{(x^1 - x_i^1 \sqrt{\sigma})^2}{2\sigma} \right) \cdot \mathrm{Exp} - \left( \frac{(x^2 - x_i^2 \sqrt{\sigma})^2}{2\sigma} \right). \quad (5)$$

28. The method according to claim 17 further comprising displaying the average acoustic energy $\tilde{P}$ ($x, t_1, t_2$) on a display device.

29. The method according to claim 17 further comprising determining an average acoustic energy over a plurality of successive time intervals, each average acoustic energy being determined using an algorithm involving at least one of the signals $P(x_i, t)$.

30. The method according to claim 29 further comprising sequentially displaying on a display device a representation of each determined average acoustic energy.

31. The method according to claim 17 further comprising determining an average acoustic energy over a plurality of successive time intervals, each average acoustic energy being determined using an algorithm involving at least one of the signals $P(x_i, t)$.

32. The method according to claim 17 further comprising:
subjecting the signals $P(x_i, t_1, t_2)$ to band pass filtering in each of one or more frequency bands; and
determining the average acoustic energy function for each frequency band based upon at least one of the filter signals.

33. The method according to claim 32 further comprising displaying one or more of the average acoustic energy functions determined for a frequency band on a display device.

34. A program storage device readable by machine, tangibly embodying a program of instructions executable by the machine to perform method steps for analyzing sounds originating in at least a portion of an individual's cardiovascular system, comprising:
processing N initial signals $P(x_i, t)$, where N is an integer, the initial signals being indicative of pressure waves at a location $x_i$; for i=1 to N, so as to generate filtered signals in which at least one component of the signals $P(x_i, t)$ not arising from cardiovascular sounds has been removed and determining an average acoustic energy $\tilde{P}$ ($x, t_1, t_2$) arising from the cardiovascular system at at least one position x over a time interval from a first time $t_1$ to a second time $t_2$, $\tilde{P}$ being determined in an algorithm involving at least one of the processed signals, wherein the average acoustic energy $\tilde{P}$ over a time interval from $t_1$ to $t_2$ is determined at a location $x_i$ of a transducer using the algebraic expression:

$$\tilde{P}(x_i, t_1, t_2) = \int_{t1}^{t2} P^2(x_i, t) dt.$$

35. A computer program product comprising a computer useable medium having computer readable program code embodied therein for analyzing sounds originating in at least a portion of an individual's cardiovascular system, comprising:

processing N initial signals $\tilde{P}(x_i, t)$, where N is an integer, the initial signals being indicative of pressure waves at a location $x_i$, for i=1 to N, so as to generate filtered signals in which at least one component of the signals $P(x_i, t)$ not arising from cardiovascular sounds has been removed and determining an average acoustic energy $\tilde{P}$ ($x, t_1, t_2$) arising from the cardiovascular system at at least one position x over a time interval from a first time $t_1$ to a second time $t_2$, $\tilde{P}$ being determined in an algorithm involving at least one of the processed signals, wherein the average acoustic energy $\tilde{P}$ over a time interval from $t_1$ to $t_2$ is determined at a location $x_i$, of a transducer using the algebraic expression:

$$\tilde{P}(x_i, t_1, t_2) = \int_{t1}^{t2} P^2(x_i, t) dt.$$

* * * * *